United States Patent
Burklow et al.

(10) Patent No.: US 6,214,381 B1
(45) Date of Patent: Apr. 10, 2001

(54) METHAZOLAMIDE COMPOSITION AND METHOD OF USE

(75) Inventors: Eddie R. Burklow, Marietta; Jeffrey S. Kiel; Jeffrey H. Ping, both of Gainesville, all of GA (US)

(73) Assignee: Effcon, Inc., Marietta, GA (US)

( * ) Notice: Subject to any disclaimer, the term of this patent is extended or adjusted under 35 U.S.C. 154(b) by 0 days.

(21) Appl. No.: 09/149,776

(22) Filed: Sep. 8, 1998

(51) Int. Cl.$^7$ .................................. A61K 9/22; A61K 9/52
(52) U.S. Cl. .................... 424/468; 424/457; 424/465; 424/470; 514/770; 514/772.3; 514/777; 514/778; 514/781; 514/784; 514/785; 514/960; 514/961
(58) Field of Search ........................ 424/468, 465, 424/470, 452, 457; 514/960, 961, 964

(56) References Cited

U.S. PATENT DOCUMENTS

| | | | |
|---|---|---|---|
| 4,259,314 | 3/1981 | Lowey | 424/19 |
| 4,357,469 | 11/1982 | Schor | 536/91 |
| 4,369,172 | 1/1983 | Schor et al. | 424/19 |
| 4,389,393 | 6/1983 | Schor et al. | 424/19 |
| 4,540,566 | 9/1985 | Davis et al. | 424/22 |
| 4,617,186 | 10/1986 | Schäfer et al. | 424/78 |
| 4,663,322 | 5/1987 | Beyer, Jr. | 514/222 |
| 4,734,285 | 3/1988 | Alderman | 424/468 |
| 4,775,535 | 10/1988 | Lowey | 424/468 |
| 4,795,327 | 1/1989 | Gaylord et al. | 424/468 |
| 4,851,232 | 7/1989 | Urquhart et al. | 424/469 |
| 4,855,143 | 8/1989 | Lowey | 424/468 |
| 4,871,548 | 10/1989 | Edgren et al. | 424/488 |
| 4,946,685 | 8/1990 | Edgren et al. | 424/472 |
| 4,983,398 | 1/1991 | Gaylord et al. | 424/465 |
| 5,009,897 | 4/1991 | Brinker et al. | 424/469 |
| 5,104,887 | 4/1992 | Schoenwald et al. | 514/367 |
| 5,126,145 | 6/1992 | Evenstad et al. | 424/465 |
| 5,157,044 | 10/1992 | Schoenwald et al. | 514/363 |
| 5,225,424 | 7/1993 | Schoenwald et al. | 514/363 |
| 5,232,705 | 8/1993 | Wong et al. | 424/473 |
| 5,283,065 | 2/1994 | Doyon et al. | 424/467 |
| 5,348,746 | 9/1994 | Dong et al. | 424/473 |
| 5,366,738 | 11/1994 | Rork et al. | 424/473 |
| 5,393,765 | 2/1995 | Infeld et al. | 514/365 |
| 5,419,918 | 5/1995 | Lundberg | 424/490 |
| 5,422,116 | 6/1995 | Yen et al. | 424/427 |
| 5,458,887 | 10/1995 | Chen et al. | 424/464 |
| 5,585,243 | 12/1996 | Aster et al. | 435/7.21 |
| 5,776,489 | 7/1998 | Preston et al. | 424/451 |

FOREIGN PATENT DOCUMENTS

| | | |
|---|---|---|
| 0201057B1 | 12/1992 | (EP) . |
| 0501678B1 | 5/1996 | (EP) . |
| 5-065227 | 9/1993 | (JP) . |

OTHER PUBLICATIONS

"Formulating for Controlled Release with Methocel Premium Cellulose Ethers," The Dow Chemical Company, Form No. 198–1029–1089AMS, pp. 1–33 (1989).

"How to Improve Pharmaceutical Formulations with Methocel Premium and Ethocel Premium Cellulose Ethers," The Dow Chemical Company, Form No. 192–961–490AMS (1990).

"Methocel Cellulose Ethers Technical Handbook," The Dow Chemical Company, Form No. 192–1062–791JB, pp. 1–37 (1988).

*Primary Examiner*—James M. Spear
(74) *Attorney, Agent, or Firm*—Sutherland Asbill & Brennan LLP

(57) ABSTRACT

A pharmaceutical composition useful for treating ocular conditions, such as glaucoma. In particular, the pharmaceutical composition is a sustained release oral dosage composition for relieving intraocular pressure comprising methazolamide and a high molecular weight binder, wherein the composition provides sustained rate of methazolamide release in an in vitro drug release profile. A filler and a lubricant may also be included.

24 Claims, 9 Drawing Sheets

METHAZOLAMIDE COMPOSITION AND METHOD OF USE

FIELD OF THE INVENTION

The present invention relates to the field of pharmaceutical compositions useful for treating ocular conditions, such as glaucoma. In particular, the pharmaceutical compositions contain methazolamide in a sustained release, oral dosage form.

BACKGROUND OF THE INVENTION

Ocular conditions characterized by intraocular pressure, such as chronic open-angle glaucoma or secondary glaucoma, have been successfully treated by administration of methazolamide, and analogs and derivatives thereof. Methazolamide is a carbonic anhydrase inhibitor that slows the formation of excess fluids behind the cornea, by inhibiting a chemical reaction at the ciliary body.

Many prior art methazolamide compositions are administerable topically, directly to the eye. Such administration can be disadvantageous to individuals who prefer oral medications. Moreover, in topical applications, the concentration of methazolamide available to the affected tissue is difficult to regulate and maintain. The frequent necessity for re-application of topical methazolamide can be inconvenient and result in inconsistent efficacy.

Additionally, some prior art methazolamide compositions provide an oral dosage of methazolamide, but these compositions do not provide a consistent dosage of methazolamide over an extended period of time. Methazolamide is a water-insoluble, hydrophilic drug. Sustained release formulations of water-insoluble hydrophobic drugs tend to yield inconsistent drug release profiles which make it difficult to control in vivo absorption of these types of drugs in the intestines.

Various controlled release pharmaceutical formulations have been proposed in the prior art, however, none have proven economical for manufacture and satisfactory in drug release profiles. Also, some of these formulations include additional compounds, such as anionic surfactants, which are undesired. Prior art formulations of sustained release methazolamide tablets have only been achieved for dosages of methazolamide in the range of 25 to 50 mg per tablet. These prior art formulations of extended release tablets have used spherical granules of methazolamide, different types of binders, or additional compounds, but none have produced a consistent drug release profile for methazolamide having methazolamide dosages of 75 mg or more per tablet.

Prior art formulations of sustained release methazolamide tablets have used lower dosages of methazolamide, from 25 to 50 mg per tablet, in the form of spherical granules which are then tableted. While tablets comprising spherical granules are effective at these lower dosage amounts, it has been difficult to achieve or control the release of the drug in higher dosage tablets having these spherical granules. Thus, there are currently no available oral methazolamide compositions containing higher dosages, i.e. at least 75 mg, in a sustained release per diem formula. Due to the low dosages in the existing prior art formulations, the tablets must be taken several times a day, which may be problematic should the individual forget to take the oral dosage at the prescribed time. Therefore, there exists a need for a sustained release methazolamide composition that contains a higher dosage of methazolamide such that only one tablet per day is required to provide relief from intraocular pressure.

A sustained release oral dosage formula is therefore desirable to provide a therapeutic concentration of methazolamide over an extended period of time without the use of unnecessary compounds. The formula would be preferably chosen such that an individual only requires a single dosage per diem. This dosage would be preferably provided in an orally administerable tablet.

SUMMARY OF THE INVENTION

A single-dosing sustained release oral dosage composition for relieving intraocular pressure is provided. These compositions comprise from about 75 to about 500 mg of methazolamide and a high molecular weight binder. The compositions are prepared such that they provide a sustained rate of methazolamide drug release in vivo. This enables an individual to relieve intraocular pressure simply by taking a single dose of methazolamide per diem. Additionally, the composition may include fillers, lubricants and/or flow agents.

Preferably, the composition comprises from about 10 to about 80 percent by weight of methazolamide; from about 1 to about 60 percent by weight of the high molecular weight binder; from about 0 to about 5 percent by weight of a lubricant; and from about 10 to about 90 percent by weight of a filler and/or flow agent. More preferably, the composition comprises about 40 percent by weight of methazolamide; about 5 percent by weight of hydroxypropyl methylcellulose; from about 1 to about 2 percent by weight of magnesium stearate; and from about 53 to about 54 percent by weight of lactose.

DETAILED DESCRIPTION OF THE INVENTION

Figure 1:
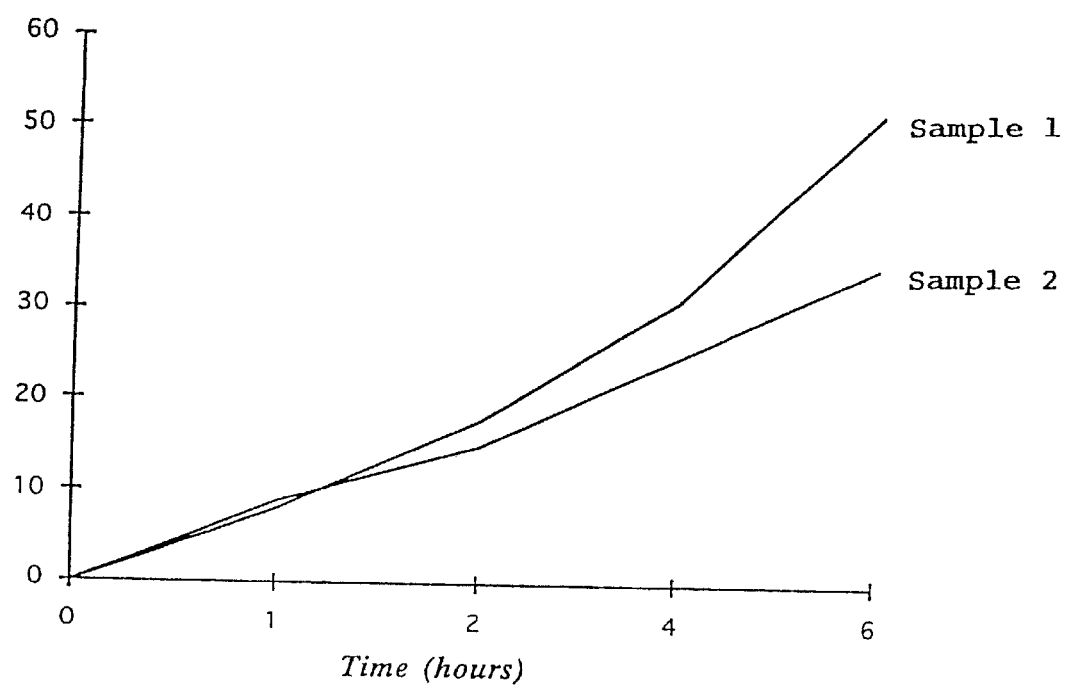
FIG. 1 shows a drug release profile for one embodiment of the invention.

A single-dosing sustained release oral dosage composition for relieving intraocular pressure is provided. These compositions comprise from about 75 to about 500 mg of methazolamide and a high molecular weight binder. The compositions are prepared such that they provide a sustained rate of methazolamide drug release in vivo. This enables an individual to relieve intraocular pressure simply by taking a single dose of methazolamide per diem. Additionally, the composition may include fillers, lubricants and/or flow agents.

Preferably, the compositions comprise from about 100 to about 150 mg of methazolamide. Also, preferably, the high molecular weight binder comprises hydroxypropyl methylcellulose having a number average weight greater than about 50,000 Daltons and more preferably about 70,000 Daltons. Preferably, the hydroxypropyl methylcellulose has a methoxyl content of about 28–30% and a hydroxypropyl content of about 7–12% and has a viscosity of about 10,000 cps in a 2% solution of water at about 20° C.

Preferably, the composition comprises from about 10 to about 80 percent by weight of methazolamide; from about 1 to about 60 percent by weight of the high molecular weight binder; from about 0 to about 5 percent by weight of a lubricant; and from about 10 to about 90 percent by weight of a filler and/or flow agent. More preferably, the composition comprises about 40 percent by weight of methazolamide; about 5 percent by weight of hydroxypropyl methylcellulose; from about 1 to about 2 percent by weight of magnesium stearate; and from about 53 to about 54 percent by weight of lactose.

Preferably, the compositions of the present invention have an in vitro drug release profile, such that from about 5 to about 30% of the methazolamide is released in the first hour; from about 40 to about 70% of the methazolamide is released after six hours; and greater than about 70% of the methazolamide is released after twelve hours. More preferably, from about 5 to about 20% of the methazolamide is released in the first hour; from about 45 to about 70% of the methazolamide is released after six hours; and greater than about 80% of the methazolamide is released after twelve hours. These drug release profiles were determined using the testing procedure set forth in Example 6. These drug release profiles help to ensure that the methazolamide will be delivered in a sustained release manner such that a person need only take a single dose per diem in order to relieve intraocular pressure. If, after six hours, less than 40% of the methazolamide has been released, then the methazolamide is being released too slowly and the person may not be experiencing relief from the intraocular pressure. However, if greater than 70% of the drug is released after six hours, then the methazolamide is being released too quickly and the person may be required to take an additional dose later that day.

Methazolamide is the active ingredient in the inventive compositions. The invention contemplates that active methazolamide analogs and derivatives thereof can also be used. Methazolamide is widely used in the treatment of ocular conditions, where lowering intraocular pressure is likely to be of therapeutic benefit, such as in chronic open-angle glaucoma, secondary glaucoma, and pre-operatively in acute angle-closure glaucoma where lowering the intraocular pressure is desired before surgery. Methazolamide is a carbonic anhydrase inhibitor that slows the formation of excess fluids behind the cornea, by inhibiting a chemical reaction at the ciliary body. Methazolamide is generally represented by the formula:

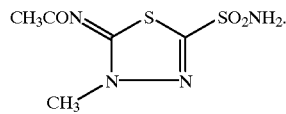

As used herein, "methazolamide" may be that obtained by any source and includes all derivatives and analogs thereof which are effective at relieving intraocular pressure.

The present invention provides oral dosage methazolamide compositions in a sustained release form, useful for treating ocular conditions, such as glaucoma. Preferably, the invention provides compositions comprising from about 75 to about 500 mg of methazolamide which may be obtained under the tradename ZOPTIC™ tablets from Effcon Laboratories, Inc. (Marietta, Ga.). The pharmaceutical compositions of the present invention preferably comprise methazolamide and hydroxypropyl methylcellulose (HPMC) in a formulation which provides an approximately consistent drug release profile over a greater than six hour time period. The formulations of the present invention can additionally include a filler, such as lactose, and a lubricant, such as magnesium stearate. The formulas preferably do not include any additional compounds, such as anionic surfactants, nor are they required to be in the form of spherical granules.

Surprisingly, the formulations of the present invention produce an approximately consistent drug release profile using formulations having the methazolamide and a high molecular weight binder, such as HPMC, wherein the formulation contains a larger dosage of methazolamide. The drug release profile ensures that methazolamide is being released over an extended period of time.

Hydroxypropylmethyl cellulose (HPMC) is preferably used as the binder to control the release of the methazolamide in a sustained release binder. Preferably, the HPMC used is a higher molecular weight HPMC. Lower molecular weight HPMCs have lower viscosities which result in faster drug release of the tablet and quicker drug release profiles. High molecular weight HPMC for use in the present invention has a number average molecular weight greater than about 50,000 Daltons (D). The present invention provides, for example, that the HPMC is METHOCEL™ E-10 HPMC (available from Dow Chemical Company) which acts as a binder sustaining the release of the active ingredient, methazolamide. METHOCEL™ E-10 has a viscosity in a 2% solution in $H_2O$ at 20° C. of about 10,000 centipoise (cps) and has a number average molecular weight of about 70,000 D. METHOCEL™ E-10 has a methoxyl content of about 28–30% and a hydroxypropyl content of about 7–12%. However, other higher molecular weight binders may be used, including, but not limited to, ethylceflulose, methylcellulose, sodium carboxymethylcellulose, hydroxypropyl cellulose, microcrystalline cellulose, starch, polyvinylpyrrolidone, sodium alginate, xantham gum and polyethylene glycols.

Fillers may be added as a diluent to achieve the appropriate total tablet weight and hardness. Fillers useful in the present invention include, but are not limited to, lactose, microcrystalline cellulose, dextrose, calcium phosphate, calcium sulfate, sucrose, mannitol, and starch. The preferred filler is lactose.

Lubricants may be added to reduce friction, prevent tablet binding, and aid in the flow of mixture during the tableting process. Lubricants useful in the present invention include, but are not limited to, magnesium stearate, calcium stearate, zinc stearate, polyethylene glycol, sodium benzoate, sodium acetate, stearic acid, talc, hydrogenated vegetable oils, and starch. The preferred lubricant is magnesium stearate.

Flow agents may be added to maximize the efficiency of the manufacturing process by facilitating the movement of the particles through the tablet-forming equipment. Flow agents useful in the present invention include, but are not limited to, lactose, talc, silicon dioxide, polyethylene glycol, microcrystalline cellulose, sodium phosphate and calcium phosphate.

The amount of methazolamide included in each tablet is preferably between 75 and 500 mg and more preferably between 100 and 250 mg. The exact amount is selected such that the compositions of the present invention preferably provide a single-dosing of methazolamide per diem. By "single-dosing" it is meant an amount of methazolamide such that an effective amount of the drug will be released over a greater than six hour period such that an individual need only take a single dosage per diem. This eliminates the need for an individual to take multiple dosages throughout the day, as is required with the current low dosage methazolamide tablets.

In one embodiment, the invention provides a pharmaceutical composition for treating an ocular condition comprising:

| Ingredients | Percentage | mg/Tablet | mg/Tablet |
|---|---|---|---|
| Methazolamide | 40 | 100 | 150 |
| Magnesium stearate | 1.55 | 3.88 | 5.81 |
| METHOCEL ™ E-10 (HPMC) | 5 | 12.5 | 18.75 |
| Lactose | 53.45 | 133.62 | 200.44 |
| TOTAL | 100 | 250 | 375 |

These are preferred dose proportional formulations giving desirable drug release profiles. These formulations provide an approximately consistent release of methazolamide for about a twelve hour period. However, other formulations have been envisioned, which will also provide an approximately consistent release of methazolamide over an extended period of time.

Preferably, the envisioned formulas of the present invention include from about 10 to about 80 percent by weight of methazolamide, from about 1 to about 60 percent by weight of a high molecular weight binder, from about 0 to about 5 percent by weight of a lubricant, and from about 0 to about 90 percent by weight of fillers and/or flow agents. More preferably, the compositions contain from about 30 to about 50 percent by weight of methazolamide, from about 3 to about 10 percent by weight of a high molecular weight binder, from about 1 to about 2 percent by weight of a lubricant, and from about 50 to about 75 percent by weight of fillers and/or flow agents.

The invention provides that sustained release methazolamide containing compositions can preferably be made by mixing the pre-weighed dry ingredients in a blender, and granulating with an 80% isopropanol (IPA) solution. The wet mass is spread thinly (approximately one-half inch) over a tray and dried at about 40° C. for approximately 10–12 hours. The dried mass is then ground to a powder, reblended, and compressed into tablets. The size of the tablets is dependent on the amount of methazolamide in the tablet and the amount of the other compounds used. Preferably, the tablets are between 100 and 750 mg each. More preferably, tablets having 100 mg of methazolamide should be about 250 mg, while tablets having 150 mg of methazolamide should be about 375 mg.

The sustained release methazolamide containing compositions can be made using other modifications to the process including, but not limited to, using a wet granulation fluid other than 80% IPA solution, such as water, methanol, ethanol, or methylene chloride. Also, different processes can be used to produce a sustained release methazolamide product such as, but not limited to, transdermal adsorption technology, and implant technology.

In alternative embodiments, certain additional excipients may be provided as flow agents in at the dry mixing stage, including lactose, polyethylene glycol (PEG), microcrystalline cellulose, sodium phosphate, or calcium phosphate. These additional compounds may be added in the amount of about 2 to about 20 percent by weight. However, only excipients which do not adversely affect the sustained drug release profile may be used. Examples of compounds that should not be added include anionic surfactants since they produce tablets which disintegrate and therefore have quicker drug release profiles. Other compounds which should be avoided include pre-gelatinized starch, croscarmalose sodium, and sodium starch glycolate.

Although tablets are the preferred oral dosage form for the methazolamide compositions of the present invention, this invention contemplates that the compositions may also be included in hard gel capsules, soft gel capsules, and the like.

The following examples outline the extreme ranges for each varied excipient. Each example reports only the lowest and highest concentration used, however, many formulations were developed within each group reported.

EXAMPLES

Example 1

The compositions described in Examples 1–5 herein were manufactured by a wet granulation method. All ingredients were weighed, based on either 100 or 150 mg methazolamide, and added to a blender. The powder was wet granulated with purified water, dried, milled, and formed into tablets. This method produced tablets with suitable compressibility characteristics, but possessed inconsistent drug release profiles. Because of inconsistent drug release results, the wet granulation fluid was changed from purified water to an 80% isopropanol (IPA) solution and a final dry blending step was added. By granulating with the IPA solution and adding another blending step, the tablets possessed the desired compressibility characteristics and consistent drug release profiles.

The acceptable and preferred in vitro drug release profiles for the following Examples can be quantified by the following ranges % label claim of drug dissolved per specific time:

| Time | Acceptable Profiles | Preferred Profiles |
|---|---|---|
| 1 hour | 5%–30% | 5%–20% |
| 6 hours | 40%–70% | 45%–70% |
| 12 hours | ≧70% | ≧80% |

The preferred method of manufacture for the compositions of the present invention is as follows:

1) All ingredients are weighed 2) All ingredients are added to a blender 3) The mixture is wet granulated with an 80% IPA solution 4) The wet mass is dried 5) The dried mass is milled 6) The milled powder is blended 7) The blended powder is compressed into tablets In the embodiment of Example 1, the following components were combined as described above:

| Ingredient | % (range) |
|---|---|
| Methazolamide | 40.0% |
| HPMC | 1.0%–15.43% |
| Lactose | 43.02%–57.45% |
| Magnesium Stearate | 1.55% |

Example 2

In the embodiment of Example 2, the following components were combined as described above:

| Ingredient | % (range) |
|---|---|
| Methazolamide | 40.0% |
| HPMC | 5.0%–7.5% |
| Lactose | 33.45–51.45% |
| Magnesium Stearate | 1.55% |
| Sodium phosphate | 2.0%–20.0% |

Example 3

In the embodiment of Example 3, the following components were combined as described above:

| Ingredient | % (range) |
|---|---|
| Methazolamide | 40.0% |
| HPMC | 5.0% |
| Lactose | 33.45%–51.45% |
| Magnesium Stearate | 1.55% |
| Polyethylene glycol | 2.0%–20.0% |

Example 4

In the embodiment of Example 4, the following components were combined as described above:

| Ingredient | % (range) |
|---|---|
| Methazolamide | 40.0% |
| HPMC | 5.0% |
| Lactose | 45.95% |
| Magnesium Stearate | 1.55% |
| Calcium phosphate | 7.5% |

Example 5

In the embodiment of Example 5, the following components were combined as described above:

| Ingredient | % (range) |
|---|---|
| Methazolamide | 40.0% |
| HPMC | 3.0%–7.5% |
| Lactose | 7.95%–52.45% |
| Magnesium Stearate | 1.55% |
| Microcellulose | 3.0%–45.5% |

Example 6

Drug release testing was performed on several formulations to determine their specific drug release profiles. The method was based upon the current U.S. Pharmacopeia (USP) XXIII (The United States Pharmacopeial Convention, Inc., Rockville, Md., 1998) dissolution test procedure for the immediate release products. The method included the use of the USP Paddle Apparatus II at 100 rpm with acetate buffer (pH=4.5) medium with various sampling points. In the method, a tablet was dropped into the apparatus, and the amount of methazolamide dissolved in the acetate buffer solution was measured over various time periods using a UV spectrophotometric method at $\lambda=280$ nm, as is well known in the art. This method gave the following drug release profiles:

| Sample 1 | Time | % Label Claim Drug Dissolved |
|---|---|---|
| 3.0% HPMC | 1 hour | 8% |
| 40.0% Methazolamide | 2 hours | 18% |
| 1.55% Magnesium stearate | 4 hours | 31% |
| 55.42% Lactose | 6 hours | 52% |

| Sample 2 | Time | % Label Claim Drug Dissolved |
|---|---|---|
| 15.43% HPMC | 1 hour | 9% |
| 40.0% Methazolamide | 2 hours | 15% |
| 1.55% Magnesium stearate | 4 hours | 25% |
| 43.02% Lactose | 6 hours | 35% |

These results are presented in FIG. 1.

Effective embodiments of the present invention are those formulations wherein the methazolamide is slowly released over a greater than six hour time period, preferably over a 12 to 16 hour period. As can be seen, both samples are effective sustained-release methazolamide formulations. Sample 1 provides a preferred drug release profile.

Example 7

A UV analysis of other specific formulations of Example 1 was performed using the method set forth in Example 6. The formulations were granulated with 80% IPA and gave the following drug release profiles:

| Sample 1 | Time | % Label Claim Drug Dissolved |
|---|---|---|
| 3.0% HPMC | 1 hour | 14% |
| 40.0% Methazolamide | 2 hours | 34% |
| 1.55% Magnesium stearate | 4 hours | 71% |
| 55.45% Lactose | 6 hours | 86% |
|  | 8 hours | 96% |
|  | 10 hours | 99% |

| Sample 2 | Time | % Label Claim Drug Dissolved |
|---|---|---|
| 5.0% HPMC | 1 hour | 9% |
| 40.0% Methazolamide | 2 hours | 15% |
| 1.55% Magnesium stearate | 4 hours | 29% |
| 53.45% Lactose | 6 hours | 39% |
|  | 8 hours | — |
|  | 10 hours | — |

Figure 2:
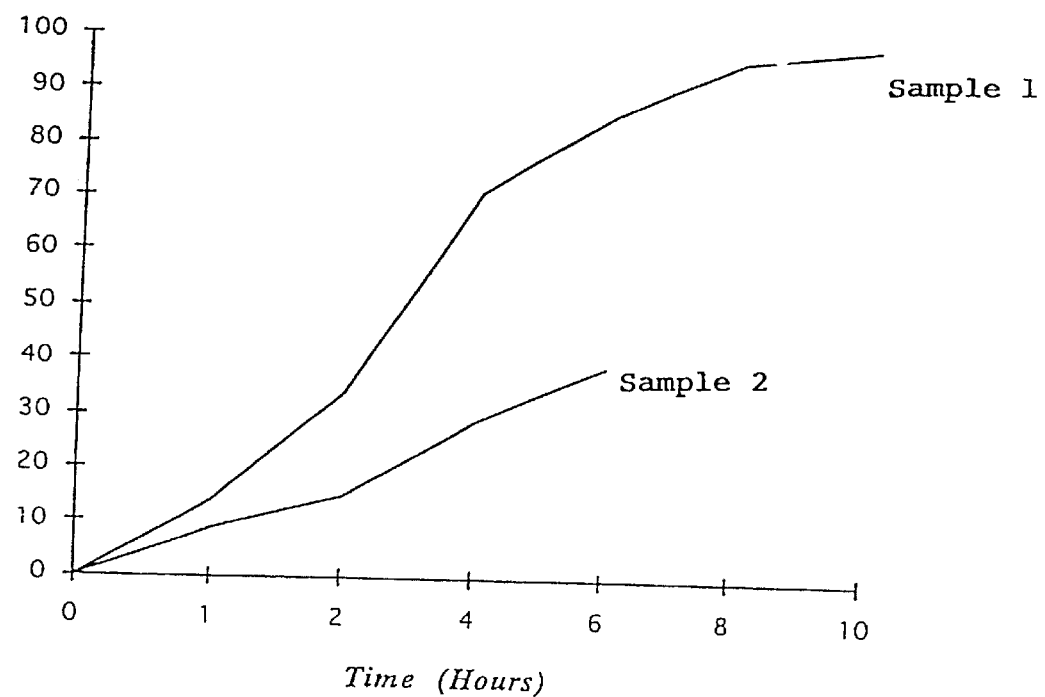
FIG. 2 shows a drug release profile for another embodiment of the invention.

These results are presented in FIG. 2.

Both samples are effective sustained-release methazolamide formulations. However, since less than 40% of the drug has been released after 6 hours, Sample 2 is less preferred.

Example 8

A UV analysis of specific formulations of Example 3 was performed using the method set forth in Example 6. The formulations were granulated with purified water and gave the following drug release profiles:

| Sample 1 | Time | % Label Claim Drug Dissolved |
|---|---|---|
| 5.0% HPMC | 1 hour | 22% |
| 5.0% PEG | 2 hours | 42% |
| 40.0% Methazolamide | 4 hours | 68% |
| 1.55% Magnesium stearate | 6 hours | 87% |
| 53.45% Lactose | | |

| Sample 2 | Time | % Label Claim Drug Dissolved |
|---|---|---|
| 7.5% HPMC | 1 hour | 8% |
| 5.0% PEG | 2 hours | 13% |
| 40.0% Methazolamide | 4 hours | 25% |
| 1.55% Magnesium stearate | 6 hours | — |
| 45.95% Lactose | | |

Figure 3:
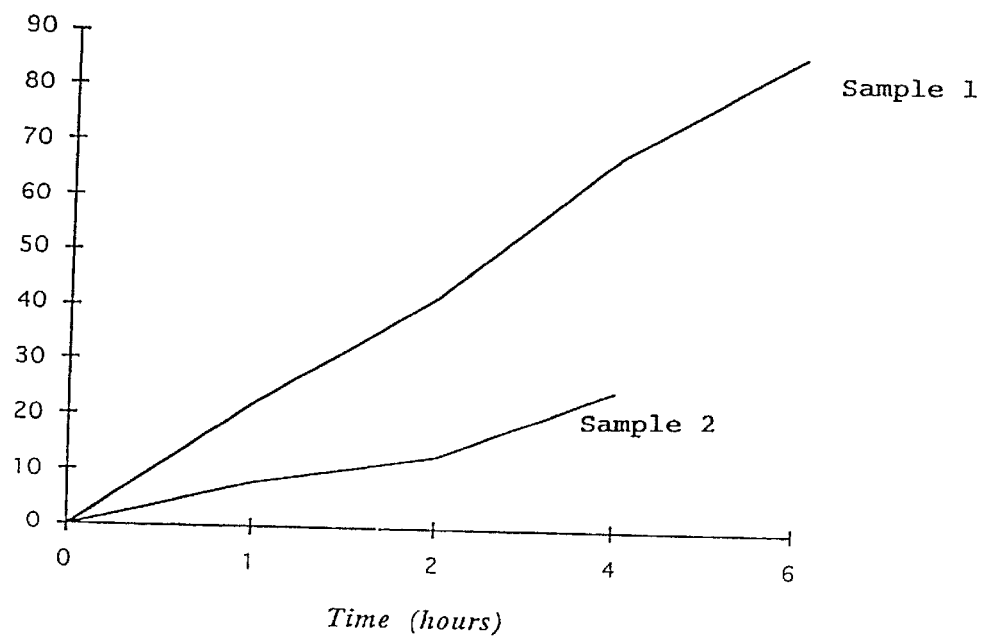
FIG. 3 shows a drug release profile for another embodiment of the invention.

These results are presented in FIG. 3.

Both samples are effective sustained-release methazolamide formulations. However, since less than 40% of the drug has been released after 6 hours, Sample 2 is less preferred.

Example 9

A UV analysis of specific formulations of Example 2 was performed using the method set forth in Example 6. The formulations were granulated with purified water and gave the following drug release profiles:

| Sample 1 | Time | % Label Claim Drug Dissolved |
|---|---|---|
| 5.0% HPMC | 1 hour | 45% |
| 2.0% $Na_3PO_4$ | 2 hours | 67% |
| 40.0% Methazolamide | 4 hours | 92% |
| 1.55% Magnesium stearate | 6 hours | 104% |
| 51.45% Lactose | | |

| Sample 2 | Time | % Label Claim Drug Dissolved |
|---|---|---|
| 7.5% HPMC | 1 hour | 16% |
| 2.0% $Na_3PO_4$ | 2 hours | 26% |
| 40.0% Methazolamide | 4 hours | 48% |
| 1.55% Magnesium stearate | 6 hours | 71% |
| 48.95% Lactose | | |

Figure 4:
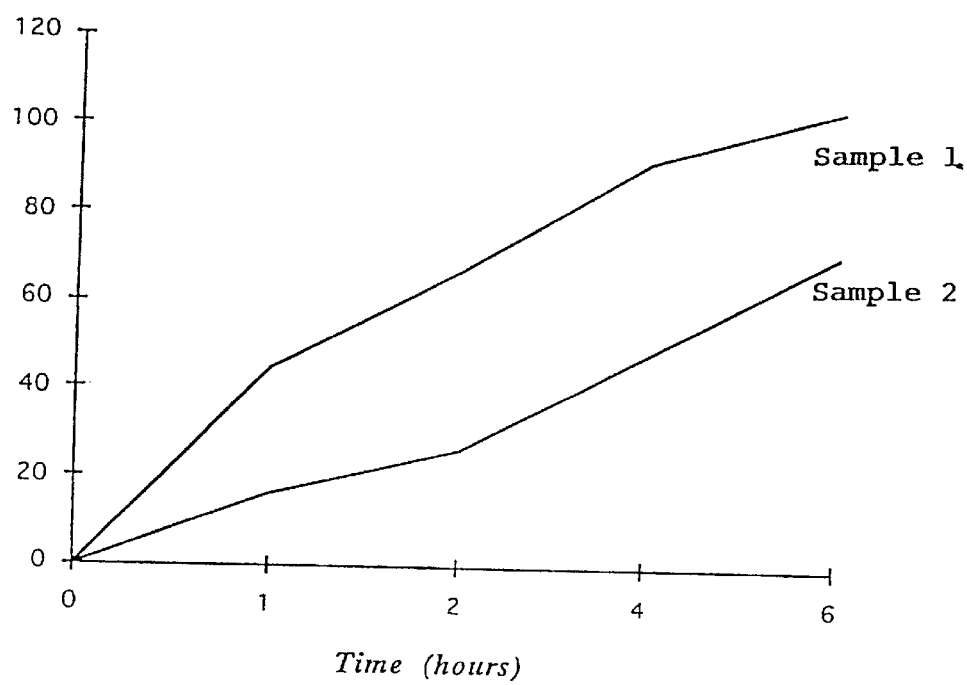
FIG. 4 shows a drug release profile for another embodiment of the invention.

These results are presented in FIG. 4.

Both samples are effective sustained-release methazolamide formulations. Sample 2 provides a desired drug-release profile. However, since all of the drug has been released after 6 hours, Sample 1 is less desirable.

Example 10

A UV analysis of a specific formulation of Example 4 was performed using the method set forth in Example 6. The formulations were granulated with 80% IPA and gave the following drug release profile:

| Sample 1 | Time | % Label Claim Drug Dissolved |
|---|---|---|
| 5.0% HPMC | 1 hour | 9% |
| 7.5% $Ca_2(PO_4)_3$ | 2 hours | 14% |
| 40.0% Methazolamide | 4 hours | 26% |
| 1.55% Magnesium stearate | 6 hours | 37% |
| 45.95% Lactose | | |

Figure 5:
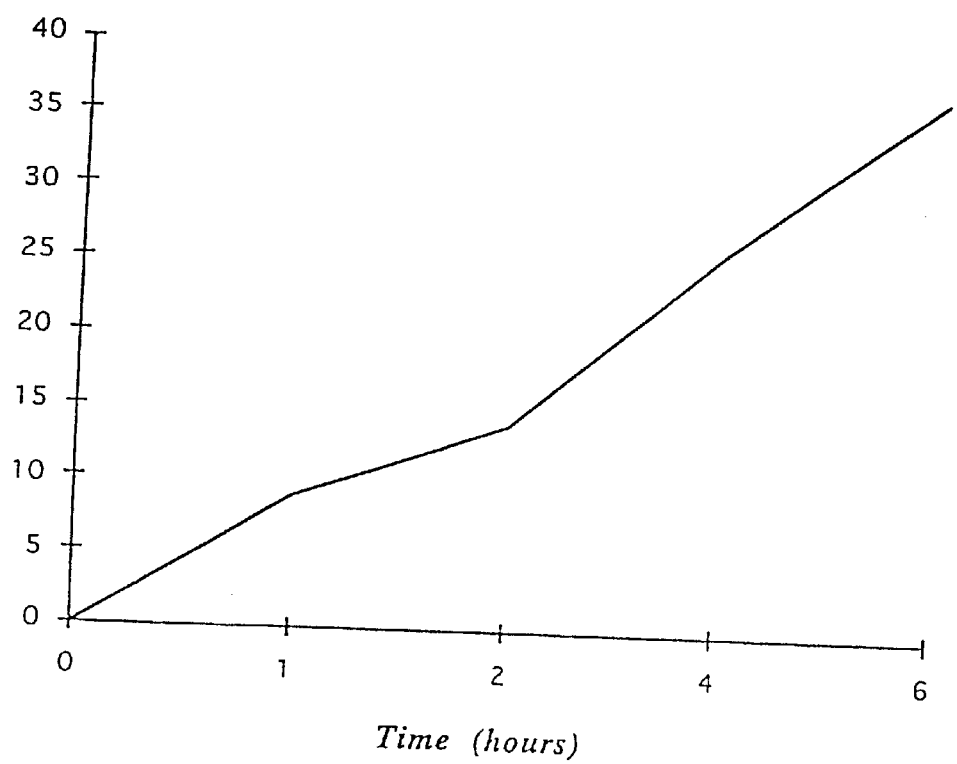
FIG. 5 shows a drug release profile for another embodiment of the invention.

These results are presented in FIG. 5.

Sample 1 is an effective sustained-release methazolamide formulation. However, since less than 40% of the drug has been released after 6 hours, this formulation is less preferred.

Example 11

A UV analysis of a specific formulation of Example 5 was performed using the method set forth in Example 6. The formulations were granulated with 80% IPA and gave the following drug release profile:

| Sample 1 | Time | % Label Claim Drug Dissolved |
|---|---|---|
| 5.0% HPMC | 1 hour | 13% |
| 10.0% microcellulose (MCC) | 2 hours | 23% |
| 40.0% Methazolamide | 4 hours | 41% |
| 1.55% Magnesium stearate | 6 hours | 59% |
| 43.95% Lactose | | |

Figure 6:
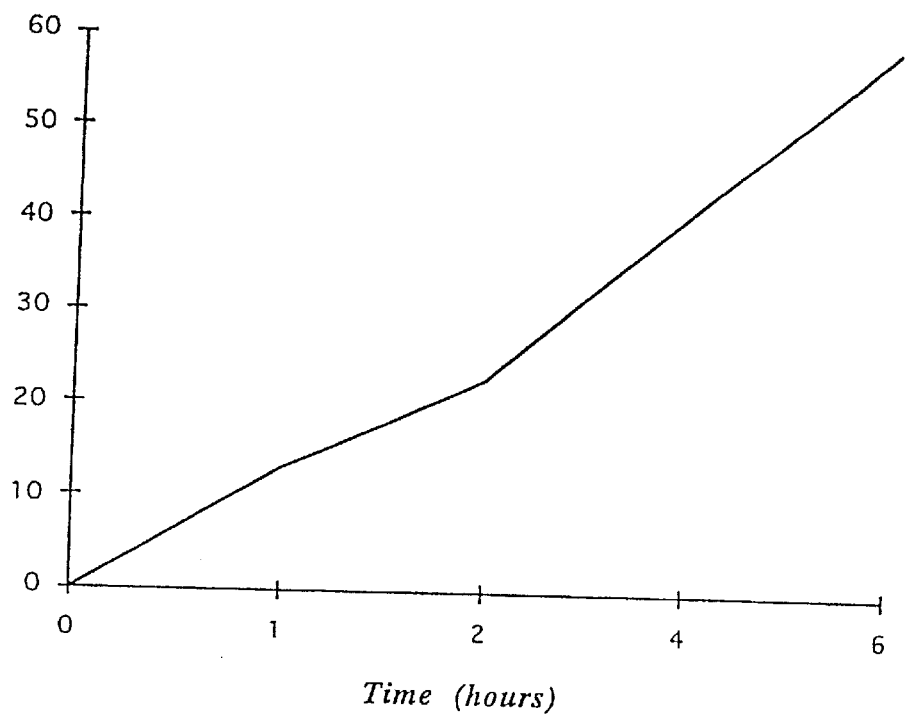
FIG. 6 shows a drug release profile for another embodiment of the invention.

These results are presented in FIG. 6.

Sample 1 exhibits a desired drug-release profile and is an effective sustained-release methazolamide formulation.

Example 12

In Example 12, one formulation of Example 1 was tested in vitro using the method set forth in Example 6, and gave the following drug release profile:

| Sample 1 | Time | % Label Claim Drug Dissolved |
|---|---|---|
| 3.0% HPMC | 1 hour | 16% |
| 40.0% Methazolamide | 2 hours | 33% |
| 1.55% Magnesium stearate | 4 hours | 60% |
| 55.95% Lactose | 6 hours | 78% |
| | 8 hours | 92% |

Figure 7:
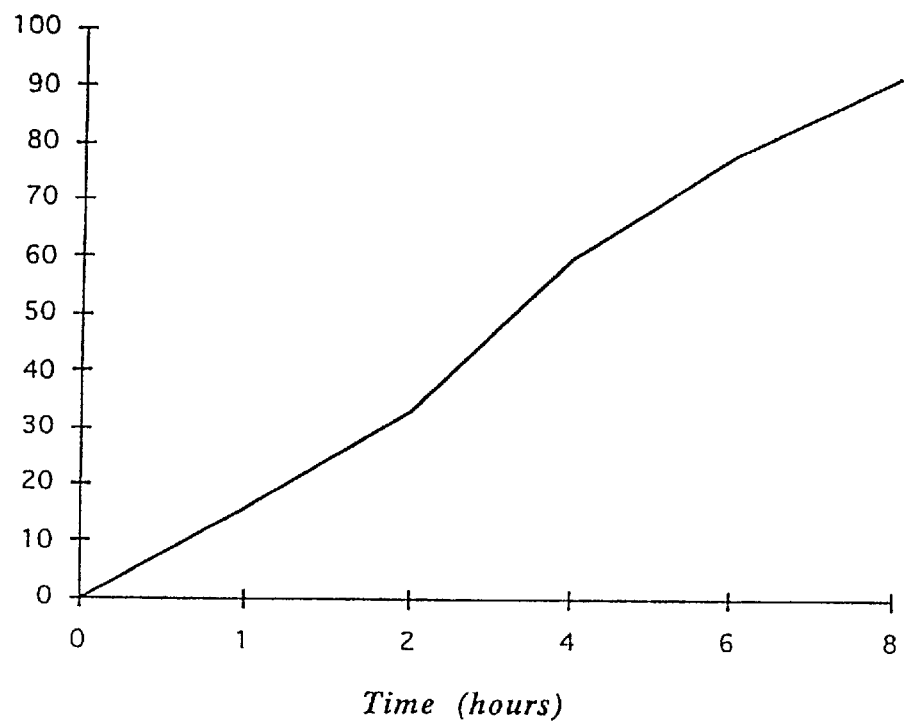
FIG. 7 shows a drug release profile for another embodiment of the invention.

These results are presented in FIG. 7.

Sample 1 is an effective sustained-release methazolamide formulation.

Example 13

In Example 13, the formulation of Example 12 was tested to determine the drug release pattern in vivo.

A sustained drug release pattern in vivo is shown mainly using three criteria:

1) $T_{max}$ (the time (after dosing) required to achieve maximum blood levels of methazolamide);

2) $C_{max}$ (the maximum blood concentration of methazolamide); and

3) $AUC_{inf}$ (the area under the curve drawn from blood concentrations of methazolamide measured at certain time periods after dosing.

The $T_{max}$ for a sustained release product should be greater than an immediate release product to demonstrate the formulation actually sustains the drug release pattern. The $C_{max}$ and $AUC_{inf}$ for a sustained release product should be comparable to that of an equivalent dose of the immediate release product to demonstrate the formulation releases all of the drug, releases the drug at a proper rate (i.e. not too slowly or too quickly), and is formulated at the proper strength. If these three criteria are met, then the sustained release formulation of the drug is acceptable.

A randomized, blinded, parallel design pilot study was conducted comparing the relative bioavailability of 150 mg Methazolamide Sustained Release Tablets (ZOPTIC™) to that of immediate release (IR) of methazolamide 50 mg tablets in normal male volunteers. Twelve subjects were randomly assigned to one of the two parallel treatment groups; 6 subjects per group. Subjects were given one of the methazolamide 150 mg SR tables or three IR methazolamide 50 mg tablets. Each subject was exposed to only one treatment and received a single oral dose of the assigned medication under fasting conditions. Blood samples were obtained within one hour prior to and at various times post-dosing.

$T_{max}$ for the immediate release product was 2.25 hours, but $T_{max}$ for ZOPTIC™ was at 4.5 hours. Clearly, the formulation for ZOPTIC™ sustained the release of methazolamide. $C_{max}$ was comparable between the immediate release product and ZOPTIC™ at 14.98 µg/mL and 14.31 µg/mL respectively. Also, $AUC_{inf}$ was comparable between the immediate release product and ZOPTIC™ at 5076.91 µg.hr/mL and 4639.64 µg.hr/mL respectively.

Figure 8:
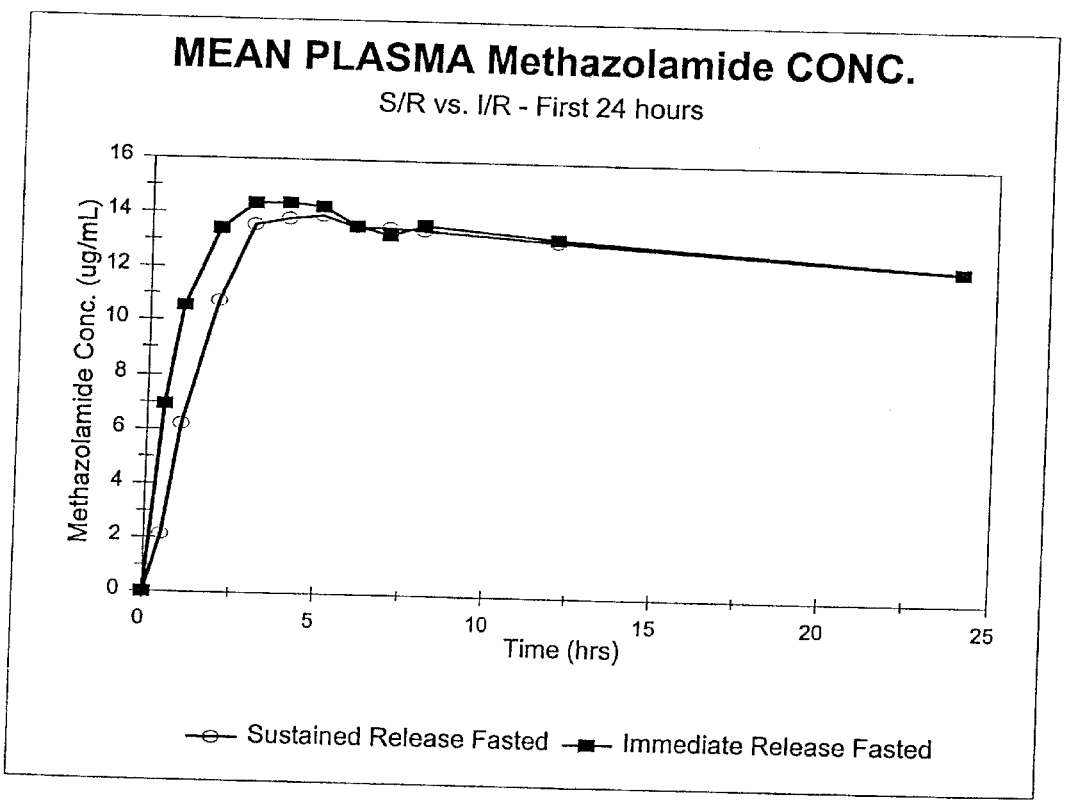
FIG. 8 shows the mean plasma concentrations of methazolamide over time for another embodiment of the invention.

The data, which is set forth in FIG. 8, demonstrate the sustained release nature of ZOPTIC™ tablets with nearly double the time required to achieve maximum blood concentrations of methazolamide when dosed equivalently with the immediate release reference product.

Example 14

A UV analysis of two preferred formulations of Example 1 was performed using the method set forth in Example 6. The formulations were granulated with 80% IPA and gave the following drug release profiles:

| Sample 1 | Time | % Label Claim Drug Dissolved |
|---|---|---|
| 12.5 mg HPMC | 1 hour | 11% |
| 100.0 mg Methazolamide | 3 hours | 36% |
| 3.75 mg Magnesium stearate | 6 hours | 68% |
| 133.75 mg Lactose | 9 hours | 95% |
|  | 12 hours | 102% |

| Sample 2 | Time | % Label Claim Drug Dissolved |
|---|---|---|
| 18.75 mg HPMC | 1 hour | 10% |
| 150.0 mg Methazolamide | 3 hours | 31% |
| 5.625 mg Magnesium stearate | 6 hours | 52% |
| 200.625 mg Lactose | 9 hours | 71% |
|  | 12 hours | 85% |

Both samples exhibit desired drug release profiles and are effective sustained-release methazolamide formulations.

Example 15

In Example 15, Sample 2 of Example 14 was tested in vivo. The results were compared to an immediate release tablet using the same methods and criteria as set forth in Example 13.

$T_{max}$ for the immediate release product was 4.10 hours, but $T_{max}$ for Sample 2 was at 7.09 hours. Clearly, the Sample 2 formulation sustained the release of methazolamide. $C_{max}$ was comparable between the immediate release product and Sample 2 at 21.72921 µg/mL and 19.53626 µg/mL respectively. Also, $AUC_{inf}$ was comparable between the immediate release product and Sample 2 at 6448.50517 µg.hr/mL and 6241.94963 µg.hr/mL respectively.

Figure 9:
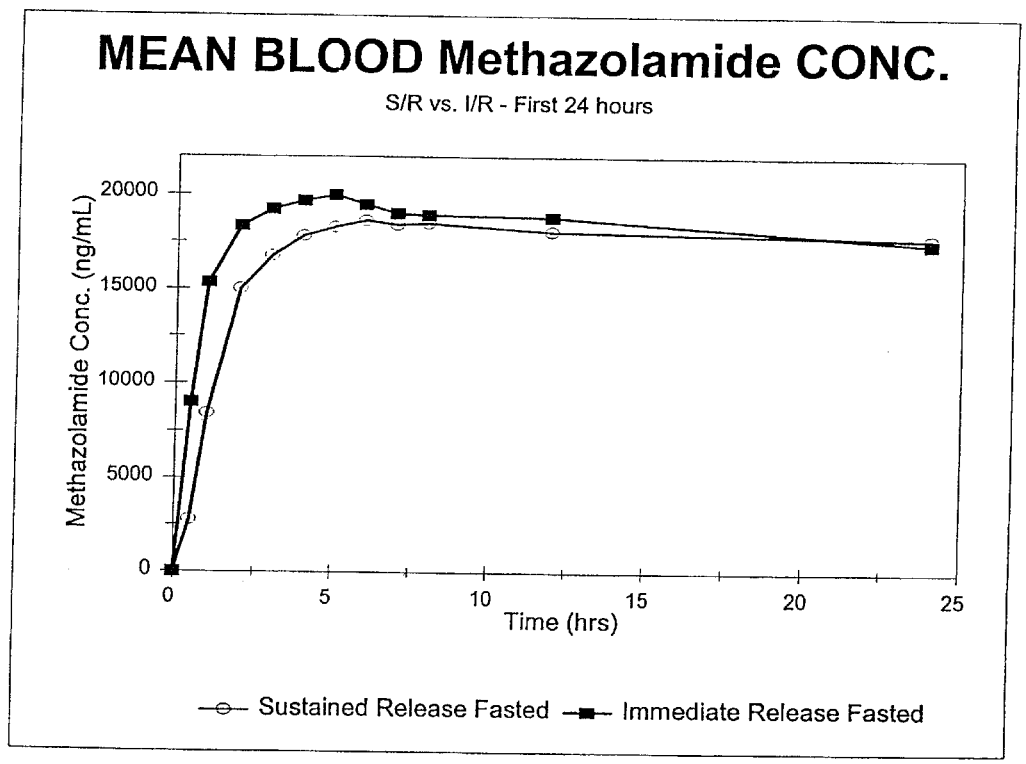
FIG. 9 shows the mean blood concentrations of methazolamide over time for another embodiment of the invention.

The data, which is set forth in FIG. 9, demonstrate the sustained release nature of the Sample 2 formulation with nearly double the time required to achieve maximum blood concentrations of methazolamide when dosed equivalently with the immediate release reference product.

The Examples herein are intended to be demonstrative of certain embodiments of the invention, and not limiting on the scope of the appended claims.

We claim:

1. A sustained release oral dosage tablet for relieving intraocular pressure comprising:
   a) about 40 percent by weight of methazolamide;
   b) about 5 percent by weight of hydroxypropyl methylcellulose having a number average molecular weight of about 70,000 Daltons and a methoxyl content of about 28–30% and a hydroxypropyl content of about 7–12%;
   c) from about 1 to about 2 percent by weight of magnesium stearate; and
   d) from about 53 to about 54 percent by weight of lactose;
   wherein the composition has an in vitro drug release profile, such that from about 5 to about 20% of the methazolamide is released after one hour; from about 45 to about 70% of the methazolamide is released after six hours; and greater than about 80% of the methazolamide is released after twelve hours.

2. The composition of claim 1, wherein the composition contains from about 75 to about 500 mg of methazolamide.

3. A sustained release oral dosage composition for relieving intraocular pressure comprising:
   a) from about 10 to about 80 percent by weight of methazolamide;
   b) from about 1 to about 60 percent by weight of a high molecular weight binder;
   c) from about 0 to about 5 percent by weight of a lubricant; and
   d) from about 10 to about 90 percent by weight of a filler and/or a flow agent;
   wherein the composition has an in vitro drug release profile, such that from about 5 to about 30% of the methazolamide is released after one hour; from about 40 to about 70% of the methazolamide is released after six hours; and greater than about 70% of the methazolamide is released after twelve hours,
   wherein the high molecular weight binder is hydroxypropyl methylcellulose having a number average molecular weight of greater than about 50,000 Daltons.

4. The composition of claim 3, wherein the composition comprises:
   a) from about 30 to about 50 percent by weight of methazolamide;
   b) from about 3 to about 10 percent by weight of the binder;

c) from about 1 to about 2 percent by weight of the lubricant; and d) from about 50 to about 75 percent by weight of the filler and/or flow agent.

5. The composition of claim 3, wherein the hydroxypropyl methylcellulose has a number average molecular weight of about 70,000 Daltons and has a methoxyl content of about 28–30% and a hydroxypropyl content of about 7–12%.

6. A single-dosing sustained release oral dosage composition for relieving intraocular pressure comprising a high molecular weight binder and from about 75 to about 500 mg of methazolamide wherein the composition has an in vitro drug release profile, such that from about 5 to about 30% of the methazolamide is released after one hour; from about 40 to about 70% of the methazolamide is released after six hours: and greater than about 70% of the methazolamide is released after twelve hours; wherein the high molecular weight binder is hydroxypropyl methylcellulose having a number average molecular weight of greater than about 50,000 Daltons.

7. The composition of claim 6, wherein the hydroxypropyl methylcellulose has a number average molecular weight of about 70,000 Daltons.

8. A single-dosing sustained release oral dosage composition for relieving intraocular pressure comprising a high molecular weight binder and from about 75 to about 500 mg of methazolamide, wherein the composition has an in vitro drug release profile, such that from about 5 to about 30% of the methazolamide is released after one hour; from about 40 to about 70% of the methazolamide is released after six hours; and greater than about 70% of the methazolamide is released after twelve hours; wherein the high molecular weight binder is hydroxypropyl methylcellulose and wherein the hydroxypropyl methylcellulose has a methoxyl content of about 28–30% and a hydroxypropyl content of about 7–12%.

9. A single-dosing sustained release oral dosage composition for relieving intraocular pressure comprising a high molecular weight binder and from about 75 to about 500 mg of methazolamide, wherein the composition has an in vitro drug release profile, such that from about 5 to about 30% of the methazolamide is released after one hour; from about 40 to about 70% of the methazolamide is released after six hours; and greater than about 70% of the methazolamide is released after twelve hours; wherein the high molecular weight binder is hydroxypropyl methylcellulose and wherein the hydroxypropyl methylcellulose has a viscosity of about 10,000 cps in a 2% solution of water at about 20° C.

10. The composition of claim 6, further comprising a lubricant, wherein the lubricant is selected from the group consisting of magnesium stearate, calcium stearate, zinc stearate, polyethylene glycol, sodium benzoate, sodium acetate, stearic acid, talc, hydrogenated vegetable oils, and starch.

11. The composition of claim 10, wherein the lubricant is magnesium stearate.

12. The composition of claim 6, further comprising a filler, wherein the filler is selected from the group consisting of lactose, microcrystalline cellulose, dextrose, calcium phosphate, calcium sulfate, sucrose, mannitol, and starch.

13. The composition of claim 12, wherein the filler is lactose.

14. The composition of claim 6, further comprising from about 2 to about 20 percent by weight of a flow agent, wherein the flow agent is selected from the group consisting of lactose, talc, silicon dioxide, polyethylene glycol, microcrystalline cellulose, sodium phosphate and calcium phosphate.

15. The composition of claim 14, wherein the flow agent is lactose.

16. The composition of claim 6, wherein the composition has an in vitro drug release profile, such that from about 5 to about 20% of the methazolamide is released after one hour; from about 45 to about 70% of the methazolamide is released after six hours; and greater than about 80% of the methazolamide is released after twelve hours.

17. The composition of claim 3, wherein the lubricant is magnesium stearate and the filler and/or flow agent are lactose.

18. The composition of claim 3, wherein the composition contains from about 75 to about 500 mg of methazolamide.

19. The composition of claim 6, comprising about 100 mg methazolamide.

20. The composition of claim 6, comprising about 150 mg methazolamide.

21. The composition of claim 8, comprising about 100 mg methazolamide.

22. The composition of claim 8, comprising about 150 mg methazolamide.

23. The composition of claim 9, comprising about 100 mg methazolamide.

24. The composition of claim 9, comprising about 150 mg methazolamide.

* * * * *